(12) United States Patent
Landgraf et al.

(10) Patent No.: US 7,547,880 B2
(45) Date of Patent: Jun. 16, 2009

(54) DRIFT TUBE FOR AN ION MOBILITY SPECTROMETER WITH INTEGRATED GAS CHANNEL

(75) Inventors: Jürgen Landgraf, Gutenberg (DE); Jürgen Riemenschneider, Leipzig (DE)

(73) Assignee: Bruker Daltonik GmbH, Bremen (DE)

( * ) Notice: Subject to any disclaimer, the term of this patent is extended or adjusted under 35 U.S.C. 154(b) by 164 days.

(21) Appl. No.: 11/672,190

(22) Filed: Feb. 7, 2007

(65) Prior Publication Data

US 2008/0073514 A1 Mar. 27, 2008

(30) Foreign Application Priority Data

Feb. 14, 2006 (DE) ............... 10 2006 006 683

(51) Int. Cl.
*H01J 49/40* (2006.01)
(52) U.S. Cl. .................. 250/287; 250/286
(58) Field of Classification Search .......... 250/287, 250/286, 281, 282
See application file for complete search history.

(56) References Cited

U.S. PATENT DOCUMENTS

| | | | |
|---|---|---|---|
| 3,699,333 A | 10/1972 | Cohen et al. | |
| 4,390,784 A | 6/1983 | Browning et al. | |
| 4,633,083 A | 12/1986 | Knorr et al. | |
| 4,712,008 A | 12/1987 | Vora et al. | |
| 4,777,363 A | 10/1988 | Eiceman | |
| 5,021,654 A | 6/1991 | Campbell et al. | |
| 5,162,649 A | 11/1992 | Burke | |
| 5,235,182 A | 8/1993 | Avida et al. | |
| 5,280,175 A | 1/1994 | Karl | |
| 5,834,771 A | 11/1998 | Yoon et al. | |
| 7,199,362 B2 * | 4/2007 | Rockwood et al. | 250/286 |
| 2001/0032929 A1 | 10/2001 | Fuhrër et al. | |

FOREIGN PATENT DOCUMENTS

| | | |
|---|---|---|
| DE | 41 30 810 | 12/1992 |
| DE | 197 27 122 A1 | 1/1999 |
| DE | 101 55 259 C1 | 5/2003 |
| EP | 0 369 751 A1 | 5/1990 |
| EP | 0 505 216 A3 | 9/1992 |
| EP | 0 026 683 B1 | 4/2001 |
| WO | WO 2005/050159 A2 | 6/2005 |

\* cited by examiner

*Primary Examiner*—Kiet T Nguyen
(74) *Attorney, Agent, or Firm*—Law Offices of Paul E. Kudirka

(57) ABSTRACT

A drift tube for an ion mobility spectrometer is assembled from stacked tube segments and has electrodes that generate an electric drift field and are electrically contactable from the outside of the drift tube. Most of the tube segments have at least two separate apertures so that, when the segments are stacked, these apertures form a drift region and at least one integrated gas channel both of which run parallel to the axis of the drift tube. At least one tube segment is inserted into the stack in which the two apertures are connected to form a gas channel transverse to the axis of the drift tube so that the drift region is connected to the gas channel at that tube segment.

14 Claims, 7 Drawing Sheets

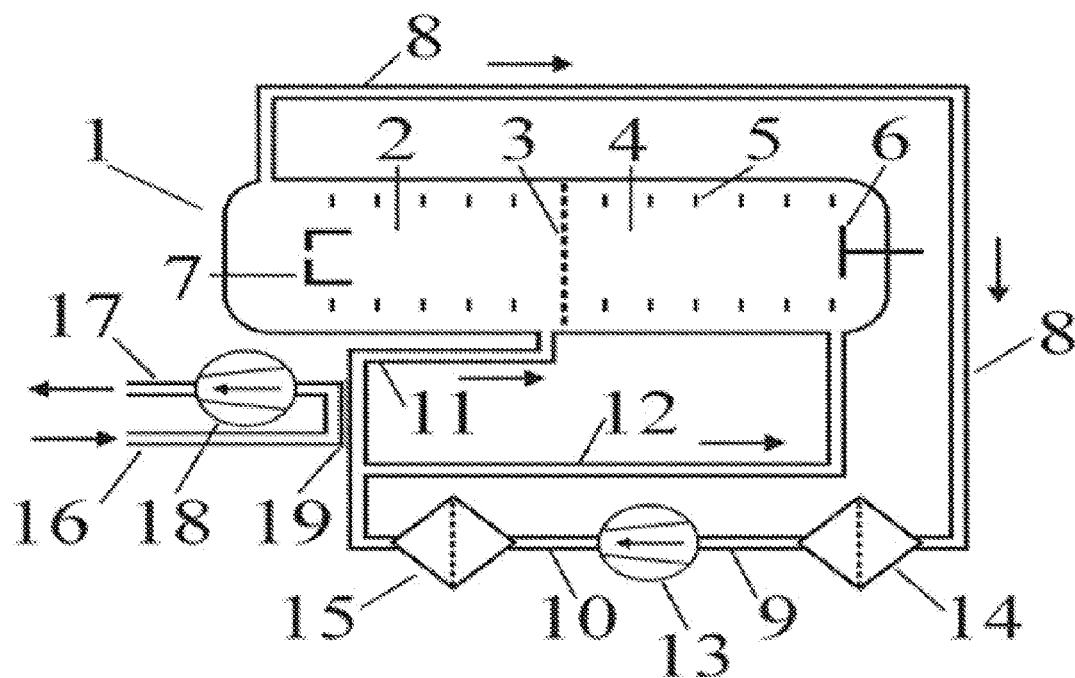
FIG. 1a *(Prior Art)*
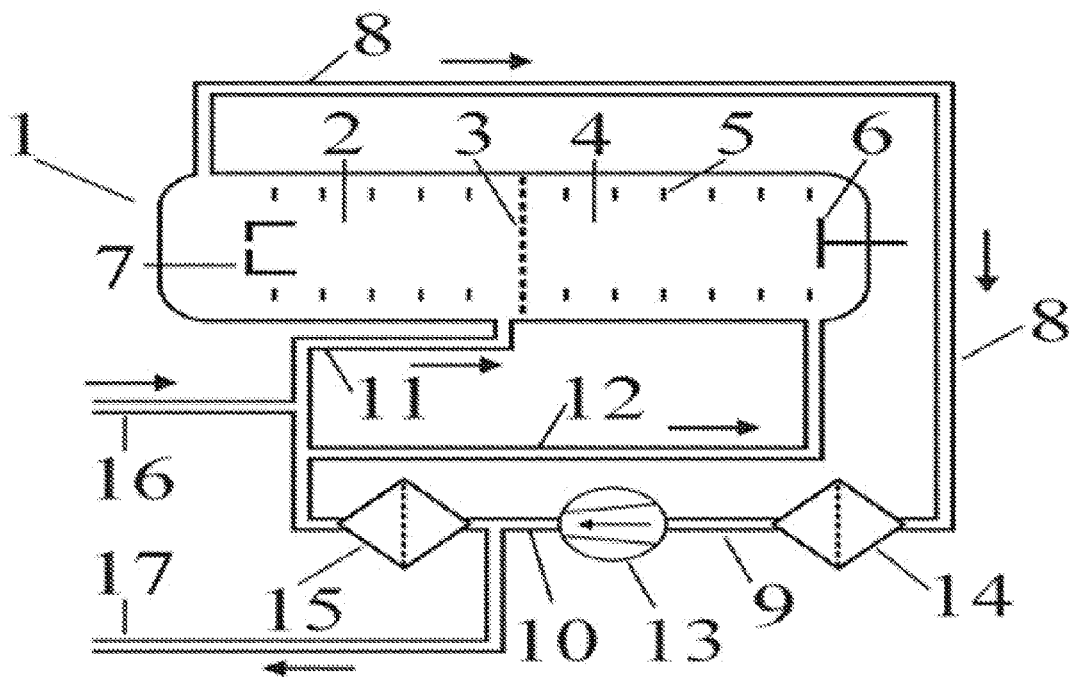
FIG. 1b *(Prior Art)*

DRIFT TUBE FOR AN ION MOBILITY SPECTROMETER WITH INTEGRATED GAS CHANNEL

BACKGROUND

The invention relates to a drift tube for an ion mobility spectrometer which is assembled from stacked tube segments and which has electrodes that generate an electric drift field and are electrically contactable from the outside of the drift tube.

Ion mobility spectrometry is a method for the highly sensitive detection of foreign substances of low concentration in ambient air or other gases. The method can be implemented as a comparatively compact arrangement and with a simple technical set-up. It is therefore particularly suited for use in portable gas analyzers and warning devices. Ion mobility spectrometry has been elucidated in U.S. Pat. No. 3,699,333 (Cohen et al.) and Pat. No. 4,777,363 (Eiceman), for example.

In ion mobility spectrometry, it is generally the mobility of ions or charged clusters in gases under the influence of an electric field which is analyzed. The mobility, taking into account gas temperature and pressure, is characteristic of the ions or charged clusters.

The most common type of ion mobility spectrometer being used at present is one with a drift tube of the time-of-flight type. In the reaction region of this type of drift tube, gas molecules are normally partially ionized by radioactive materials such as $^{63}Ni$. The ionization of the substances to be analyzed from a fed-in gas sample is typically carried out only in subsequent chemical reactions, which are influenced by gaseous water or introduced gaseous doping agents such as ammonia. In the reaction region, the ions of the substances to be analyzed drift in an axial electric drift field to a gating mechanism, e.g. a Bradbury-Nielsen shutter or a potential barrier. By briefly switching off or switching over potentials across the gating mechanism, ions are admitted as a pulsed ion current into the drift path of the drift tube, where they move in an axial electric drift field to the collecting electrode. The ion-specific mobility means that the ionic species exhibit different speeds and are temporally separated. The time delay of the ion current at the collecting electrode with respect to the opening of the gating mechanism determines the ion-specific drift times, which are a measure of the mobility of the ions. The reaction region and the drift path together form the drift region of the drift tube, in which the ions drift along an axial electric drift field in the direction of the collecting electrode.

In other types of ion mobility spectrometer such as the filter types (FAIMS="Field Asymmetric Ion Mobility Spectrometer") or the multi-electrode types (aspiration types), the ions drift in electric fields aligned radially or transverse to the axis of the drift tube. A drift gas which flows through the drift tube at right angles to the electric fields transports the ions along the axis of the drift tube.

An ion mobility spectrometer of the time-of-flight type has a pneumatic system which usually comprises the drift tube, a gas pump (gas transport system), filters and gas channels (gas connections). The gas channels connect the pneumatic components (drift tube, gas pump and filters) to form a gas circuit in which the gas is circulated by the gas pump. In order to achieve reproducible results with an ion mobility spectrometer of the time-of-flight type, in particular, the gas must be continuously cleaned and the moisture kept as constant as possible at a low level (10 to 100 parts per million). The filters clean the circulated gas by removing the substances to be analyzed which have not been ionized in the reaction region; and they extract excess moisture brought into the gas circuit by the gas sample. Inside the drift tube, the ions encounter a constant flow of gas which is thoroughly cleaned to prevent the formation of additional ions of the substances to be analyzed. To control the gas flow, the pneumatic system can also have pneumatic switching and control elements, e.g. switching valves. The sensors of the ion mobility spectrometer monitor important gas parameters such as the pressure, temperature and moisture.

Along the drift path of the drift tube an axial electric drift field has to be generated. In order to minimize any temporal broadening of the measured ion current pulse for an ionic species, the drift field should have maximum homogeneity transverse to the axis of the drift tube. A homogeneous axial electric drift field can be generated by electrically conductive ring electrodes, for example, which are arranged so as to be equidistant and concentric to the axis of the drift tube, and across which uniformly increasing electric potentials are applied (Eiceman U.S. Pat. No. 4,777,363). The field homogeneity improves with increasing ratio of the inner diameter to the separation distance of the ring electrodes. The individual potentials are usually tapped from a shared voltage divider.

In most cases, the reaction region of the drift tube is constructed like the drift region, although here the field homogeneity does not have to be as high and hence a larger separation distance or a smaller diameter of the ring electrodes can be chosen. Besides the ring electrodes, the drift tube contains a gating mechanism between the reaction region and the drift region as well as a screen grid near to the collecting electrode. All electrically conductive parts of the tube, including the ionization source located in the reaction region, must have a defined electric potential and therefore must be contactable from outside. These electrically conductive parts are termed "electrodes" below.

The drift tube of an ion mobility spectrometer of the time-of-flight type must customarily perform the following tasks:
  Sealing off the drift region from the outer region of the drift tube,
  Ionizing the gas sample in the reaction region,
  Generating a homogeneous axial electric drift field, particularly along the drift path,
  Mechanically holding the electrodes and their electrical insulation,
  Preventing the gas sample from being carried into the drift path.

To prevent an unfiltered gas sample from being carried into the drift path, the drift path is purged with cleaned drift gas, which flows from the collecting electrode to the gating mechanism and keeps the gas sample away from the drift path. The gas stream in the drift tube ensures that any outgassings which may be present are continuously flushed off the interior walls of the drift tube. It is also a requirement for the drift tube that outgassings from the drift tube itself are minimized.

An early version of a drift tube of the time-of-flight type has a support in the interior of a gas-tight container; the support mechanically holds the electrodes of the drift tube (especially the ring electrodes) and electrically insulates them from each other (Cohen et al. U.S. Pat. No. 3,699,333). The drift tube is connected to the other components of the pneumatic system via hoses or metal pipes. The electrical connection of the electrodes is made via electric feedthroughs in the gas-tight container. In order to minimize the number of expensive electrical feedthroughs, a voltage divider which provides the individual potentials for the ring electrodes can be installed in the interior of the gas-tight container. A similar version (Kyoung et al. U.S. Pat. No. 5,834,771) realizes the ring electrodes with the aid of a flexible circuit board providing metallized strips, bent into a tube, and likewise housed inside a gas-tight container.

The separate realization of the mechanical electrode holder and the sealing of the drift tube leads to a relatively large arrangement which is not particularly suitable for small, mobile instruments. Moreover, the gas-tight container must have a relatively large aperture, which must be subsequently closed, so that the support can be mounted. Furthermore, either there has to be a large number of electrical feedthroughs in the gas-tight container, or the electrical components in the interior of the drift tube, e.g. the resistors of the voltage divider or the flexible circuit board, have to be made of a material which does not outgas. Both of these are very expensive.

In another version, the ring electrodes are replaced by tubes or tube segments which are weakly electrically conductive or whose inside has a coating with low electrical conductivity (Browning et al. U.S. Pat. No. 4,390,784). A gas-tight container can be used to hold and center the tubes or tube segments (Vora et al. U.S. Pat. No. 4,712,008). This simplifies the mechanical set-up and reduces the number of electrodes for which contacts have to be made. Tube segments with an interior coating still require a certain number of electrical feedthroughs, however.

Campbell et al. (U.S. Pat. No. 5,021,654) use a monolithic ceramic block which has a coating with low electrical conductivity in the interior, and to which all other components of the drift tube are mechanically fastened. Numerous electrical contacts are fed through the wall of the ceramic block here, and it is very labor-intensive to seal them all. Moreover, the monolithic ceramic block cannot be manufactured by a method that is suitable for mass production, such as dry pressing followed by sintering, because the block has a complicated design with a large number of apertures which lead in different directions. In U.S. Pat. No. 5,021,654 a glass ceramic which can be machined in the fired state is used for the monolithic ceramic block. However, the material's porosity and high surface affinity for water make it unsuitable for an ion mobility spectrometer, which is operated under changing climatic conditions. The machining of other ceramic materials which are suitable for ion mobility spectrometers is extremely difficult in the fired state because they are so hard and brittle. Moreover, the reproducible and homogeneous coating of parts of the inside of the ceramic block with a weakly conducting material is very demanding technologically so that this design is not suitable for mass production.

Another version uses tubes which are not themselves electrically conductive but which have conductive ring electrodes on the outside or a continuous coating with low electrical conductivity (Burke U.S. Pat. No. 5,162,649; Vandrish et al. EP 0 369 751; Kaltschmidt et al. DE 197 27 122; Leon EP 0 505 216). With this version, the electrodes of the drift tube can be provided with electrical contacts from the outside without the need for expensive feedthroughs. The electric field penetrates into the interior either capacitively or as a result of leakage currents in the tube.

To monitor the ambient air for pollutants, the ions of both polarities are usually detected, a process which is effected by cyclically changing over the direction of the electric drift field at intervals of a few seconds. With the drift tubes just described, ions which reach the insulating inner wall of the tube are not neutralized but remain there as charged stationary ions and bring about a static charging of the inner wall. This charge focuses subsequent ions of the same polarity at the axis of the drift tube, so the ion current at the collecting electrode increases. If the direction of the electric drift field is changed over in order to measure ions of the other polarity, these same charges initially bring about a deflection of the ions to be detected to the inner wall of the drift tube, thus reducing the measurement signal. The signal increases until the charge reversal of the inner walls is complete. This charge reversal process takes between a few minutes and hours to stabilize and thus prevents ions of both polarities from being measured quickly. Externally coated tubes are hence only suitable for special measuring tasks where it is sufficient to detect ions of one polarity.

In another version, the drift tube is assembled from electrically conductive and insulating rings. In the direction of the axis of the drift tube, electrically conductive and insulating rings alternate. The electrically conductive rings (ring electrodes) extend from the interior of the drift tube to its exterior surface so that electrical contact can be made with each ring electrode from the outside (Knorr et al. U.S. Pat. No. 4,633,083; Eiceman U.S. Pat. No. 4,777,363; Avida et al. U.S. Pat. No. 5,235,182). The contact surfaces between the individual rings are sealed. One production method for such a drift tube consists in tightening the stacked rings mechanically from the outside by inserting sealing rings. The mechanical support required for this is an additional expense, however, and requires space, which is at a premium in small mobile instruments. Furthermore, the large number of sealed points presents a high risk of leaks. A simpler drift tube with significantly greater mechanical robustness is obtained by using metallic ring electrodes with Z-shaped cross section into which perfectly fitting insulating rings with rectangular cross section are inserted. The stacked ring electrodes and insulating rings are bonded or soldered (Karl DE 41 30 810); this creates a self-supporting, gas-tight drift tube which can be equipped with electrical contacts from the outside. Unavoidable assembly tolerances when assembling the stacked ring electrodes and insulating rings with this production method give rise to relatively large length tolerances for the finished drift tube when shrinkage of the bonded layers and soldered layers occurs.

With all types of ion mobility spectrometer up to now, the drift tube is usually connected to the pneumatic components of the ion mobility spectrometer via separate gas pipes (gas channels), such as hoses or capillaries. Producing and assembling the gas pipes of the ion mobility spectrometer represents a large proportion of the overall manufacturing cost.

In the case of the drift tubes assembled from ring electrodes and insulating rings, in particular, the gas pipes generally have to be flexible to compensate for the relatively high tolerances of the assembly and joints. To mount the flexible gas pipes, suitable adapters are integrated into the drift tube, creating more costs. The use of flexible hoses is not ideal, especially for gas analysis, as they represent an increased risk of leaks and outgassing. Moreover, impurities can enter the drift tube when hoses are being fitted, requiring additional cleaning. Compensating for the tolerance with curved and soldered metal capillaries promises better tightness, but is more expensive to manufacture and assemble, and requires additional work procedures to clean flux residues from the joints and the drift tube. Alternatively, the bonded or soldered drift tubes can be made to fit perfectly by mechanically reworking the drift tubes in the assembled state. However, clamping and aligning the drift tube is time-consuming.

Moreover, additional cleaning is again necessary to remove pollutions introduced by machining.

SUMMARY

A drift tube according to the invention is assembled from stacked tube segments, most of the tube segments having at least two separate apertures. The apertures of the stacked tube segments align to each other in such a way that, in the assembled state, they form at least one integrated gas channel in addition to a drift region, said gas channel running along the axis of the drift tube. Moreover, at least one connecting tube segment is inserted in the drift tube, said segment forming a gas channel transverse to the axis of the drift tube and connecting the drift region to a gas channel which runs along the axis of the drift tube.

The drift tube is either assembled from electrically conductive and insulating tube segments or from insulating tube segments only, the latter arrangement having a conductive layer between two insulating tube segments. The electrically conductive tube segments and the electrically conductive layers extend from the interior (drift region) to the outer region of the drift tube and serve as electrodes for generating the electric drift field. The electrodes thus have an electrical connection from the outside.

Additional connecting tube segments can form further gas channels transverse to the axis of the drift tube which connect gas channels running along the axis of the drift tube with each other, or connect the reaction region of the drift tube with the outer region of the ion mobility spectrometer. With these tube segments, there is a common gas flow through some of the apertures which form the drift region and the gas channels.

The tube segment apertures which run lengthways and transverse to the axis of the drift tube make it possible to create integrated gas channels between any points of the drift tube. It is particularly possible to merge the gas connections of the drift tube via integrated gas channels so that all external gas connections of the drift tube to the other pneumatic components can be made via a single tube segment.

Since the tolerances of the drift tube joints have no effect on the position of the gas connections within the gas connection section, it is especially possible to connect the drift tube to the pneumatic system of the ion mobility spectrometer without complex flexible gas connections. Furthermore, in the assembled state no re-machining of the drift tube and little or no cleaning is required. Integrating the gas channels into the drift tube thus makes the equipment much easier to manufacture.

The integrated gas channels of the drift tube lead preferably to a pneumatic block which is joined to the drift tube and closes off its end. The other pneumatic components such as a gas pump or filter, and sensors are also connected to the pneumatic block. The drift tube is connected to the other pneumatic components either via gas channels integrated into the pneumatic block or by separate gas connections such as metal capillaries. Installing pneumatic components and sensors to suitably shaped tube segments and the gas connection via the integrated gas channels of the drift tube means that the function of the pneumatic block can be performed partially, or even completely, by the drift tube itself.

Furthermore, special gas channels which can be opened and sealed again and which are large enough to be used as chambers for filter or doping materials can be integrated into the drift tube. The filter or doping materials are replaced after the ion mobility spectrometer has been in operation for a suitable length of time.

The drift tube is assembled from stacked tube segments whose contact surfaces are preferably flat surfaces which, in the assembled state, are aligned at right angles to the axis of the drift tube. Tube segments with planar geometry can be manufactured at low cost in large numbers using established production technologies such as dry pressing or punching.

In the assembled state, the drift region of the drift tube and the integrated gas channels to the outer region of the drift tube are sealed off from each other. According to the materials used, different jointing techniques, e.g. bonding, soldering or welding, are required. Plastics or ceramics are primarily used for the insulating tube segments, while the electrically conductive tube segments are made of metal, a conductive plastic, a conductive ceramic, a conductively coated plastic or a conductively coated ceramic.

The correct choice of material and jointing technique means that the drift tube is self supporting and gas tight. Mechanical ribbing, fastenings, electrical contact elements and/or pneumatic sealing edges can be integrated into the tube segments in such a way that electrical or pneumatic components, sensors, circuit boards or parts of the housing can be mounted directly onto the drift tube. The drift tube itself can form the mechanical support structure and, with a suitable design and coating, it can also form parts of the outer wall of the ion mobility spectrometer as well.

The invention also includes drift tubes which have more than one drift region. The tube segments here have apertures which are aligned to each other in the assembled state forming more than one drift region and at least one integrated gas channel. With this type of ion mobility spectrometer it is possible, for example, to measure ions of both polarities at the same time.

The example embodiments describe ion mobility spectrometers of the time-of-flight type. The invention is not limited to this type, however; it can be applied to all types of ion mobility spectrometer where electrodes are electrically connected from the outside and gas channels are to be integrated into the drift tube. The drift field generated by the electrodes here is not limited to an axial electric drift field which is constant over time.

BRIEF DESCRIPTION OF THE DRAWINGS

The schematic FIGS. 1a) and 1b) illustrate ion mobility spectrometers of the time-of-flight type according to the prior art with a membrane inlet or a direct inlet system.

DETAILED DESCRIPTION

Figure 2A:
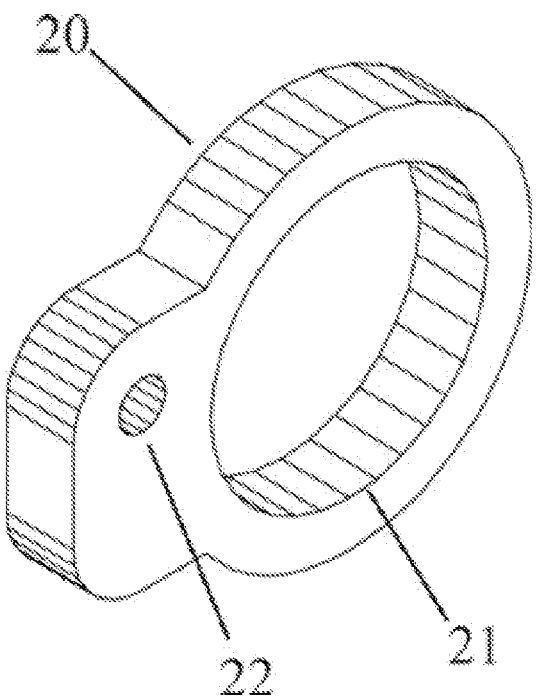
FIGS. 2a) to 2e) illustrate insulating tube segments ((20), (30), (40), (50)) and an electrically conductive tube segment (60).

While the invention has been shown and described with reference to a number of embodiments thereof, it will be recognized by those skilled in the art that various changes in form and detail may be made herein without departing from the spirit and scope of the invention as defined by the appended claims.

FIGS. 1a) and 1b) show a schematic representation of ion mobility spectrometers of the time-of-flight type. In both Figures, the drift region of the drift tube (1) comprises a reaction region (2) and a drift path (4) separated by a gating device (3). The primary ionization of gas molecules takes place in close proximity to the ionization source (7), which contains a radioactive beta emitter ($^{63}$Ni). Typically, the substances to be analyzed, which enter the reaction region (2) with the sample gas, are ionized only at the end of a complex chain of ion-ion reactions. The ions generated are drawn by an axial electric drift field in the direction of the gating device (3), where they are prevented from passing. The gating device (3) opens briefly to admit a pulse of ions into the drift path (4), where they move in an axial electric drift field to the collecting electrode (6). A substance-dependent ion current profile is measured at the collecting electrode (6) because of the different mobilities of the ions. The axial electric drift field is generated by the large number of field electrodes (5).

The ion mobility spectrometers in FIGS. 1a) and 1b) each incorporate a gas circuit in which a gas pump (13) circulates the gas in the gas circuit through the drift tube (1) and the two filters (14) and (15). Close to the ionization source (7), gas is removed by suction from the drift tube (1) and flows back into the drift tube (1) via the gas channels (8), (9), (10), (11) and (12). Cleaned gas is fed into the reaction region (2) and the drift path (4) via the gas channels (11) and (12). This creates a unidirectional gas stream in the drift tube (1) so that only cleaned drift gas flows through the drift path (4). The substances to be analyzed reach the reaction region (2) with cleaned gas via the gas channel (11). The filters (14) and (15) clean the circulating gas by removing substances to be analyzed and keep the moisture of the gas constant at a low concentration.

FIG. 1a) shows the ion mobility spectrometer separated by a semi-permeable membrane (19) from the ambient gas (membrane system). The ambient gas is drawn in by a second gas pump (18) via the gas inlet channel (16) and flows back via the gas outlet channel (17). The semi-permeable membrane (19) is thus flushed from outside with ambient gas and from inside with the gas in the gas circuit. The substances to be analyzed enter the gas channel (11) via the semi-permeable membrane (19) and flow into the reaction region (2) with the gas of the gas circuit. The semi-permeable membrane can generally be heated in order to reduce memory effects.

FIG. 1b) represents an ion mobility spectrometer with a direct inlet system. The gas inlet channel (16) opens directly into the gas channel (11) between the filter (15) and the drift tube (1), while the gas outlet channel (17) between the gas pump (13) and the filter (15) is connected to the gas circuit of the drift tube (1). The ion mobility spectrometer is thus directly connected with the ambient gas. The pressure differences where the two gas channels (16) and (17) enter mean that ambient gas to be analyzed is drawn in via the gas inlet channel (16) and gas flows out of the gas circuit via the gas outlet channel (17). The filter (15) prevents substances to be analyzed from getting into the drift path (4) of the drift tube (1) when the gas pump (13) is at a standstill. The gas channels (16) and (17) are preferably designed as capillaries.

FIGS. 2a) to 2e) illustrate four insulating tube segments ((20, (30), (40), (50)) and an electrically conductive tube segment (60). The contact surfaces of the tube segments shown are flat and parallel so that the tube segments can easily be stacked. In the stacked or assembled state the contact surfaces are aligned at right angles to the axis of the drift tube.

FIG. 2a) illustrates an insulating tube segment (20) constructed in accordance with the principles of the invention having two separate apertures (21) and (22). If the tube segment (20) is assembled with other tube segments shown, the corresponding apertures of the tube segments are aligned. The apertures (21) and (22) form the drift region of a drift tube and an integrated gas channel which runs along the axis of the drift tube, respectively.

The insulating tube segments preferably comprise an oxidic ceramic, particularly aluminum oxide ($Al_2O_3$), and are manufactured by dry pressing with subsequent sintering. Other methods of manufacture, such as ceramic injection molding, can also be used. The insulating tube segments can also be produced from a plastic as punched or injection molded parts; a suitable choice of material prevents outgassing in the drift region of the drift tube.

Figure 2B:
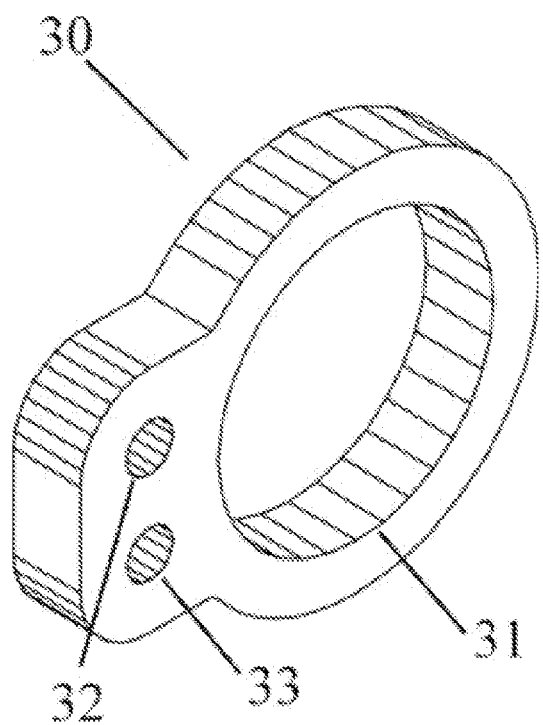

FIG. 2b) illustrates an insulating tube segment (30) having three separate apertures (31), (32) and (33). The apertures (21) and (31), and (22) and (32), are aligned in the assembled state and form the drift region and an integrated gas channel, respectively. The aperture (33) enables the formation of a second integrated gas channel which runs along the axis of the drift tube.

Figure 2C:
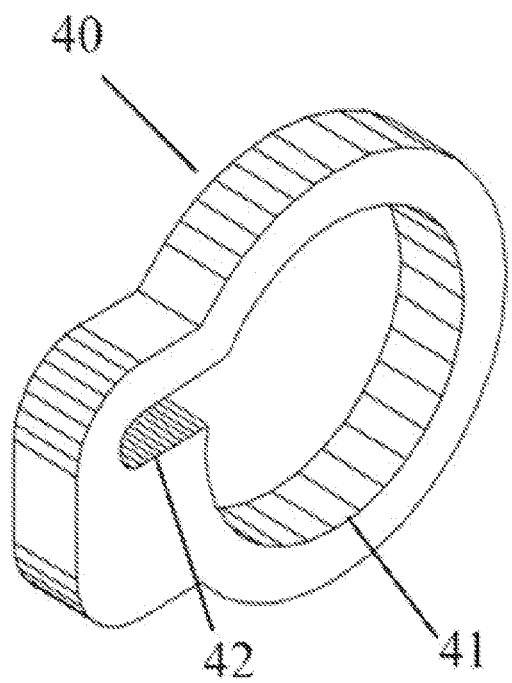
Figure 2D:
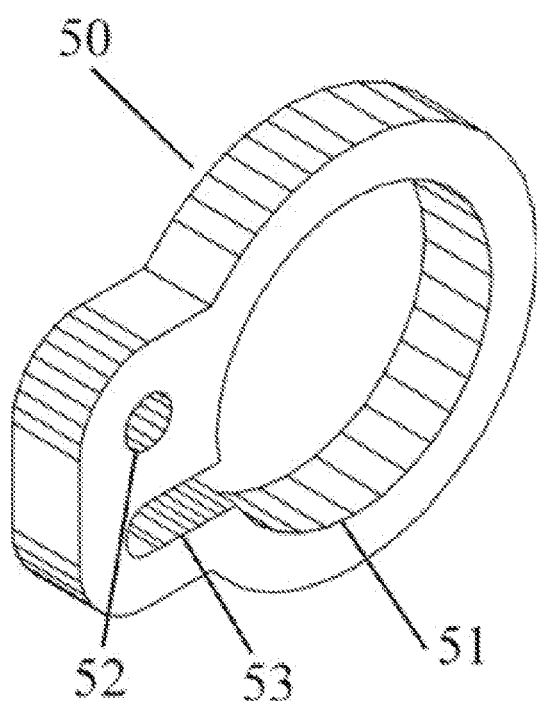

FIGS. 2c) and 2d) illustrate two connecting insulating tube segments ((40), (50)). In a modification of the tube segment (20), where the apertures (21) and (22) are separate, a notch (42) is formed in the tube segment (40). The tube segment (40) forms a gas channel transverse to the axis of the drift tube and connects the drift region with an integrated gas channel. The other connecting tube segment (50) corresponds to the tube segment (30), the apertures (31) and (33) being connected by the notch (53).

Figure 2E:
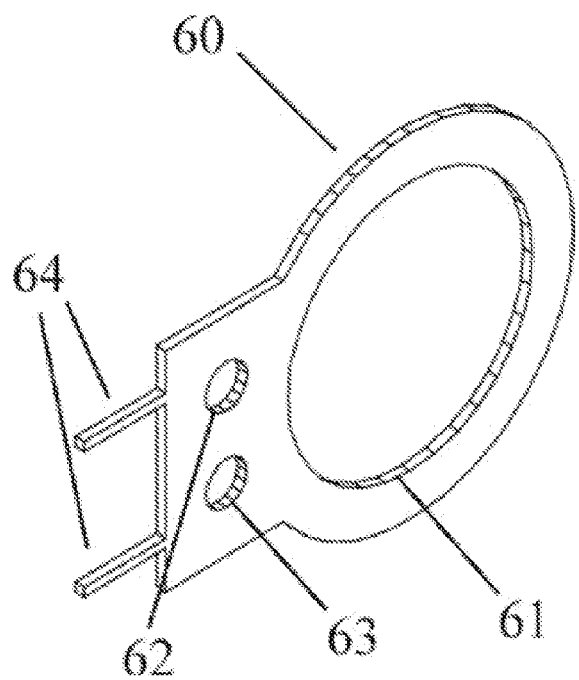

FIG. 2e) illustrates an electrically conductive tube segment (60) which is preferably made of metal. The apertures (61), (62) and (63) correspond to the apertures of the insulating tube segments shown in FIGS. 2a) to 2d). Other electrically conductive materials, such as a conductive plastic or ceramic, or a conductively coated plastic or ceramic, are also possible, however.

Figure 3A:
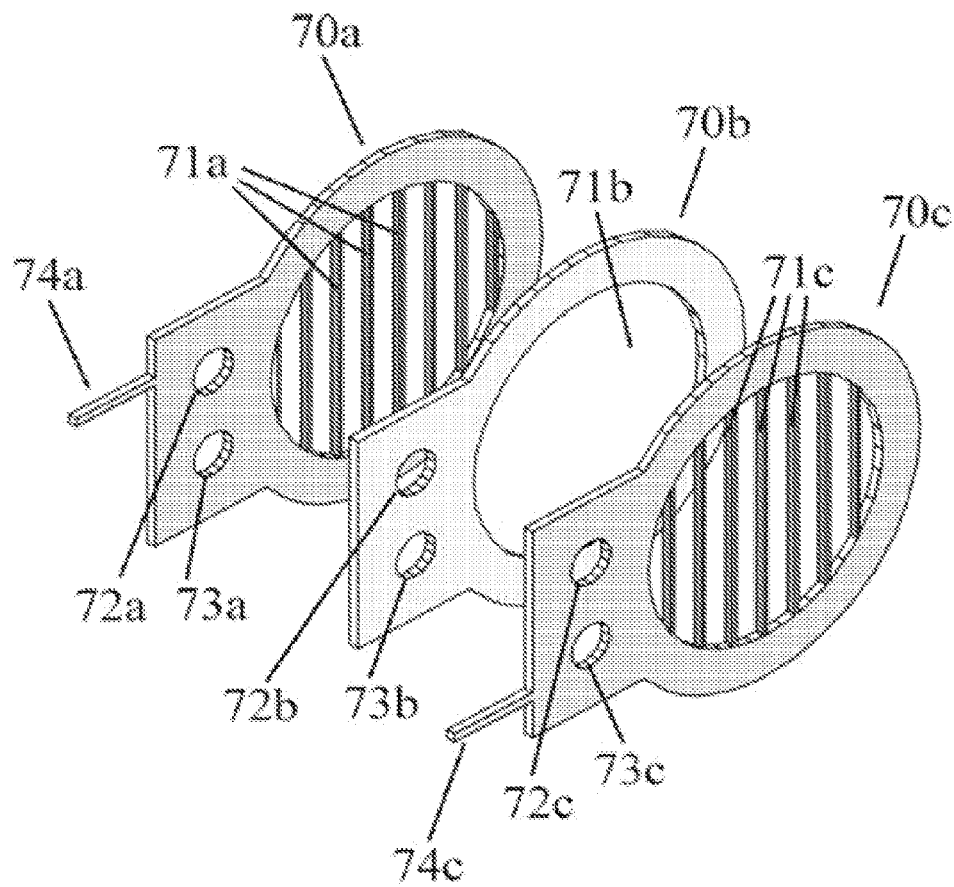
FIG. 3a) illustrates the structure of an electric gating grid (70) which is used as the gating mechanism (3) between the reaction region (2) and the drift path (4) of an ion mobility spectrometer of the time-of-flight type.
Figure 3B:
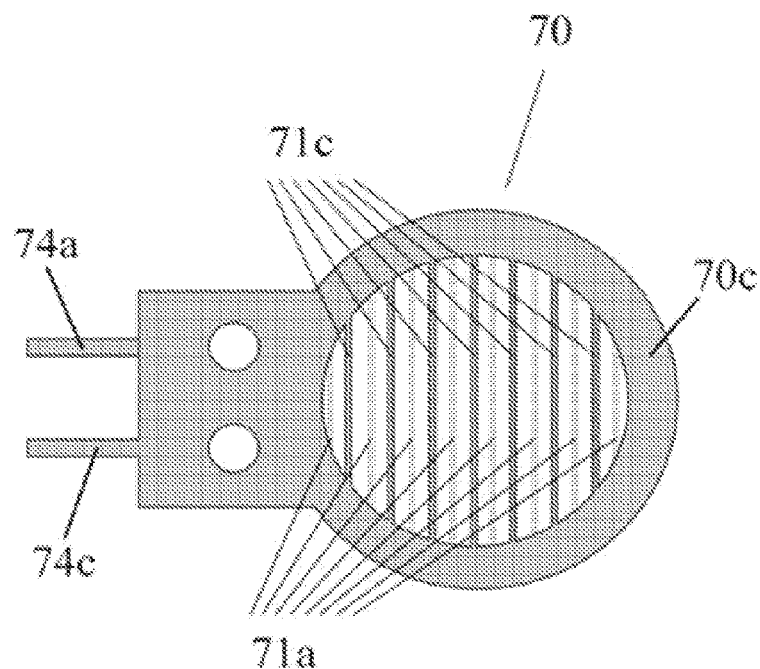
FIG. 3b) illustrates the electric gating grid in the assembled state in plan view.

FIG. 3a) shows two electrically conductive grid-shaped tube segments ((70a), (70c)) and a thin insulating tube segment (70b) which form the electric gating grid (70) when assembled. FIG. 3b) illustrates the electric gating grid (70) in the assembled state in plan view. In the assembled state, the apertures (72a), (73a), (72b), (73b), (72c) and (73c) are aligned to those apertures in the tube segments shown in FIGS. 2a) to 2e) which form the integrated gas channels along the axis of the drift tube. Aperture (71b) of the insulating tube segment (70b) is aligned to the apertures which form the drift region of the drift tube (1). The grid-shaped tube segments (70a) and (70c) have narrow parallel grid bars (71a) and (71c) in the aperture, which is aligned with the drift region; the positions of the grid bars (71a) and (71c) are offset in relation to each other so that, in the assembled state, there is always one grid bar between two grid bars of the other tube segment (see FIG. 3b).

If a blocking voltage is applied to the grid-shaped tube segments (70a) and (70c), this creates an electric field transverse to the axis of the drift tube between opposite grid bars. This field deflects ions according to their polarity to the grid bars of one of the two grid-shaped tube segments (70a) and (70b). The tube segment (70b) separates the two grid-shaped tube segments (70a) and (70c) from each other. If the voltage between the grid-shaped tube segments (70a) and (70c) is high enough, all ions are deflected and discharged at the grid bars. In this blocking case, ions cannot pass through the electric gating grid (70). Switching off the blocking voltage for a short time enables a pulse of ions to enter into the drift path (4) of the drift tube (1).

Figure 4:
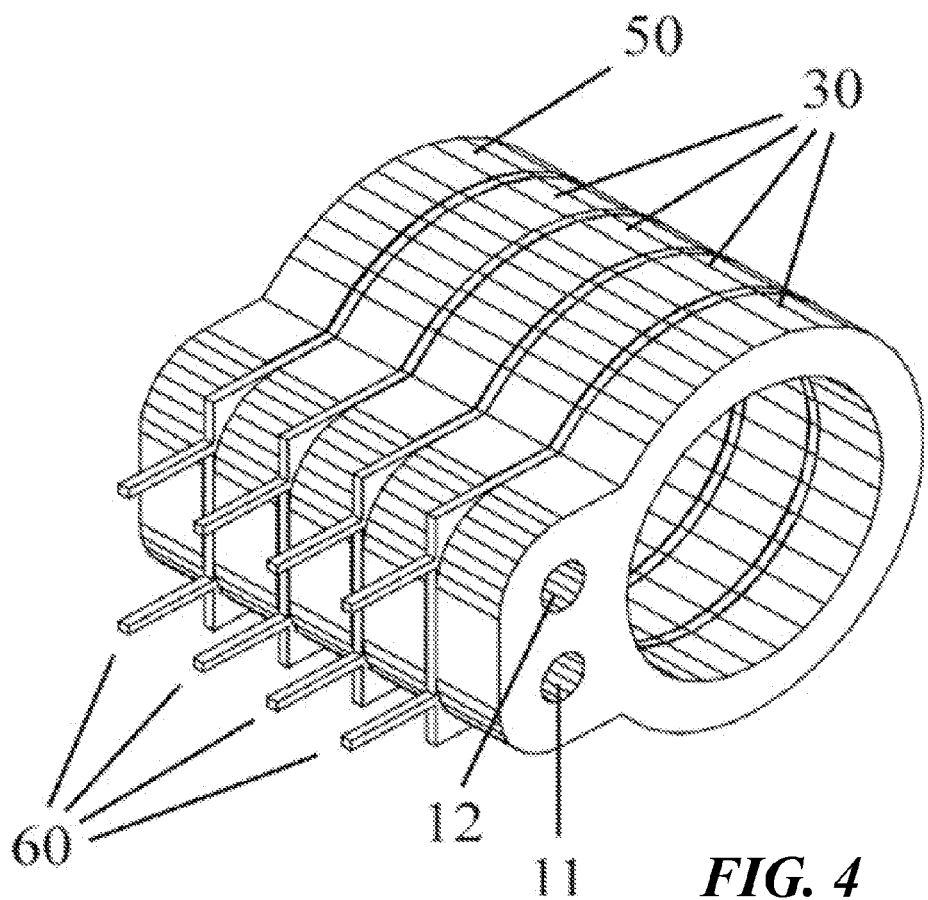
FIG. 4) illustrates a section of a drift tube of the time-of-flight type assembled from insulating tube segments ((30), (50)) and conductive tube segments (60) forming the reaction region (2) of the drift tube (1).

FIG. 4) illustrates the construction principle of a section of a drift tube (1) of the time-of-flight type assembled from insulating tube segments ((30), (50)) and electrically conductive tube segments (60). In the assembled state, the apertures (31), (51) and (61) of the corresponding tube segments form the reaction region (2) of the drift tube (1). The apertures (32), (52) and (62), and (33), (53) and (63) of the corresponding tube segments form the integrated gas channels (12) and (11) which run along the axis of the drift tube. The two integrated gas channels (11) and (12) and the reaction region (2) are sealed so as to be gas-tight apart from the notch (53) in the tube segment (50) transverse to the axis of the drift tube. The notch (53) in the tube segment (50) connects the gas channel (11) with the reaction region (2).

A single electrically conductive tube segment (60) is inserted between two insulating tube segments each time. All electrically conductive tube segments (60) have electrical contacts from the outside and generate an axial electric drift field in the reaction region (2). The electrical contacts are made by soldering the tongues (64) of the tube segments (60) preferably directly into a circuit board or by inserting them into standard push-in fittings in the 2.5 millimeter grid. In both cases it is very easy to make the contacts.

The insulating tube segments ((30), (50)) are made of ceramic and are attached to the electrically conductive metal tube segments (60) by hard soldering. The contact surfaces of the electrically conductive and insulating tube segments here are coated with a soldering paste; preferably only the insulating tube segments are coated on both sides by simple and inexpensive screen-printing. After coating, all tube segments are stacked and soldered by heating to high temperatures in inert gas or in a vacuum. The separate apertures of the tube segments are sealed off from each other by the soldering. The electrically conductive tube segments (60) preferably consist of a metal alloy whose coefficient of thermal expansion is matched to the ceramic. If the insulating tube segments are made of a plastic, these are preferably connected to the electrically conductive tube segments by adhesive bonding.

Figure 5:
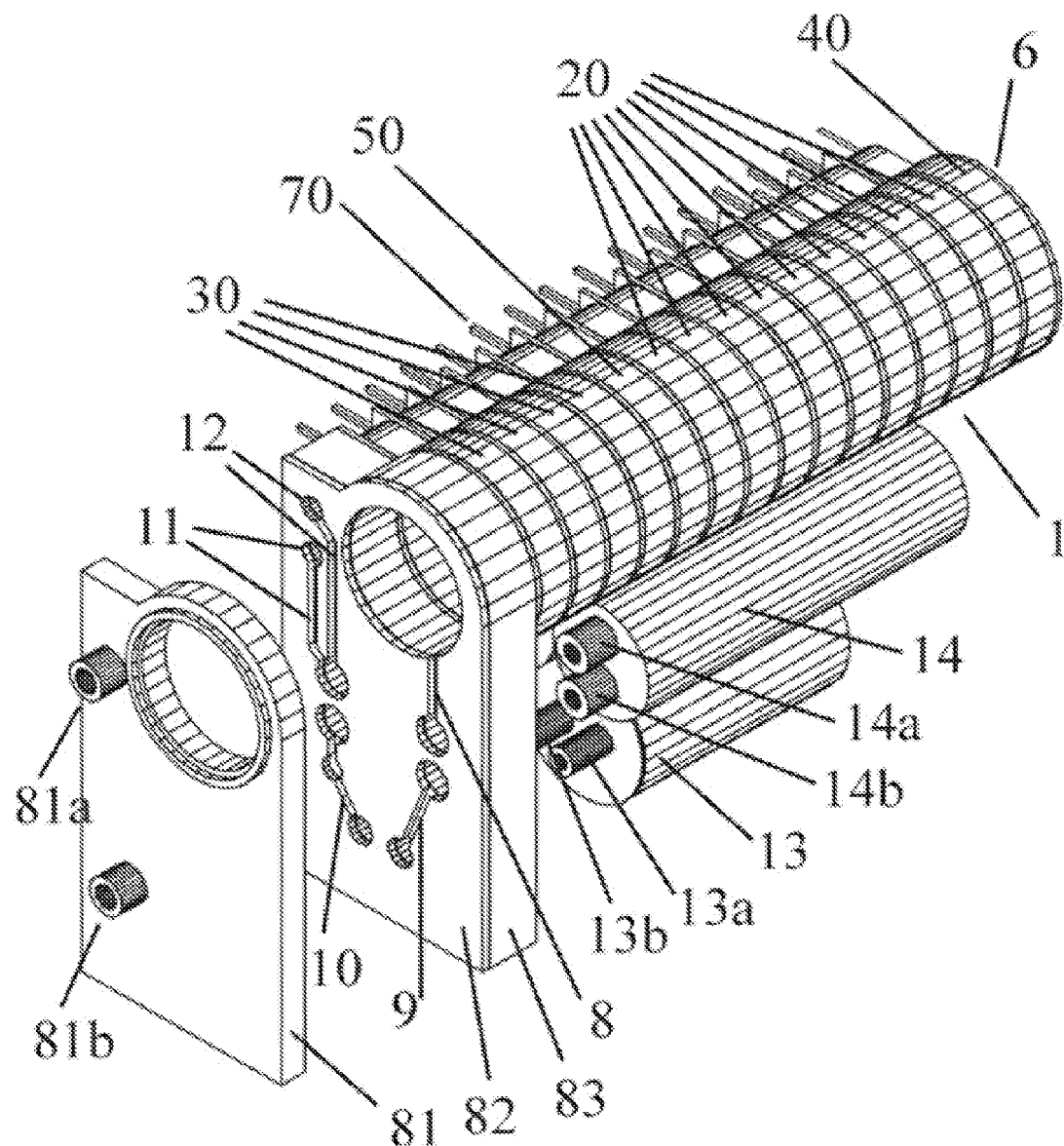
FIG. 5) illustrates an ion mobility spectrometer of the time-of-flight type with a drift tube assembled from insulating tube segments ((20), (30), (40), (50)), electrically conductive tube segments (60), an electric gating grid (70), a pneumatic block (comprising a closing plate (81), a connecting plate (82), and an interfacing plate (83)), to which the drift tube and other pneumatic components of the ion mobility spectrometer (gas pump (13), filters (14), (15)) are connected.

FIG. 5) illustrates an ion mobility spectrometer of the time-of-flight type with a drift tube (1) according to the invention. The sensors of the ion mobility spectrometer, the ionization source (7), and the electrical and electronic components and contacts are not shown. The pneumatic system corresponds to the ion mobility spectrometer in FIG. 1b).

The drift tube (1) is assembled from insulating tube segments ((20), (30), (40), and (50)), electrically conductive tube segments (60) and an electric gating grid (70). The insulating and the electrically conductive tube segments are preferably made of ceramic or metal hard-soldered with the aid of a soldering paste. In the drift tube (1), an electrically conductive tube segment is always inserted between two insulating tube segments, to be precise, the electric gating grid (70) between the insulating tube segment (50) and the first insulating tube segment (20) along the drift path (4), and otherwise electrically conductive tube segments (60). For the sake of clarity, the electrically conductive tube segments (60) are shown but not marked. The electric gating grid (70) permits brief pulsed admission of ions into the drift path (4) of the drift tube (1). All electrically conductive tube segments ((60), (70)) generate an axial electric drift field in the drift tube (1) and have electrical contacts from the outside.

The section of the drift tube (1) which forms the reaction region (2) has already been described in FIG. 4). The insulating tube segments (20) and (40) as well as the electrically conductive tube segments (60) form the drift path (4) and continue the integrated gas channel (12). The two connecting tube segments (50) and (40) connect the gas channel (11) to the reaction region (2) and the gas channel (12) to the drift path (4). The collecting electrode (6) closes off the drift tube (1) at the end of the drift path (4).

Instead of the electric gating grid (70), a conventional Bradbury-Nielsen shutter can also be used as the gating device (3) to generate a pulsed ion current. Since the two bars of a pair are insulated from each other, a Bradbury-Nielsen shutter cannot be hard-soldered to insulating tube segments with a conductive active soldering paste, but rather is adhesively bonded afterwards to the separately assembled sections of the drift tube (1) which form the reaction region (2) and the drift path (4).

The drift tube (1) is connected to a pneumatic block (comprising the closing plate (81), the connecting plate (82) and the interfacing plate (83)) to form a structural unit. All the pneumatic components (sensors, filters (14) and (15), and gas pump (13)) required to operate the ion mobility spectrometer are connected to the pneumatic block, which has connectors for this purpose. In FIG. 5), the ion mobility spectrometer is not completely assembled in order to illustrate how the pneumatic system operates: The closing plate (81) is not yet connected to the connecting plate (82); and the two filters ((14), (15)) and the gas pump (13) are not yet connected to the interfacing plate (83). The connecting plate (82) takes the form of a thin ceramic plate coated with solder paste with continuous slits which create gas channels between the pneumatic components. Both the closing plate (81) and the interfacing plate (83) are manufactured as metal parts and are soldered to the connecting plate (82) so as to be gas-tight. The interfacing plate (83) has apertures to connect the two filters (14) and (15) and the gas pump (13), which are preferably connected by means of nozzle connections sealed with O-rings. The threaded capillary joints (81a) and (81b) in the closing plate (81) are used to connect capillaries as inlet channel (16) and outlet channel (17) (corresponding to the direct inlet system in FIG. 1b)). The pneumatic block is permanently connected to the drift tube (1) via the interfacing plate (83). To connect pneumatic components, such as the interfacing plate (83), or sensors, the tube segments can also contain form elements or sealing surfaces.

The aperture in the pneumatic block which leads to the reaction region (2) of the drift tube (1) ensures access to the ionization source (7) (not shown), which is inserted into the end of the reaction region (2). This aperture is reversibly sealed with a large-area pressure sensor (not shown).

The two integrated gas channels (11) and (12) formed by the corresponding tube segments along the axis of the drift tube are continued by apertures in the interfacing plate (83) and by apertures and slits in the connecting plate (82). The gas channels (8), (9) and (10) are likewise formed by slits in the connecting plate (82). The gas channels (8) and (9) connect the reaction region (2) to the inlet (13a) of the gas pump (13). The gas is removed by suction from the reaction region (2) close to the ionization source (7) (not shown) via the gas channel (8) and flows through the filter (14) which, like the gas pump (13), is connected to the gas circuit via apertures in the plates (82) and (83). After the gas pump (13) the gas flows via the gas channel (10) into the filter (15), which is not visible because of the perspective of the illustration. At the output of the filter (15) the gas stream branches into the gas channels (11) and (12), in which the gas flows back into the drift tube (1).

If capillaries are connected to the threaded capillary joints (81a) and (81b) as inlet channel (16) and outlet channel (17), the ambient gas is drawn in directly from the outer region via the inlet channel (16) and, at the same time, gas flows out of the gas circuit via the outlet channel (17) to the outside.

Figure 6A:
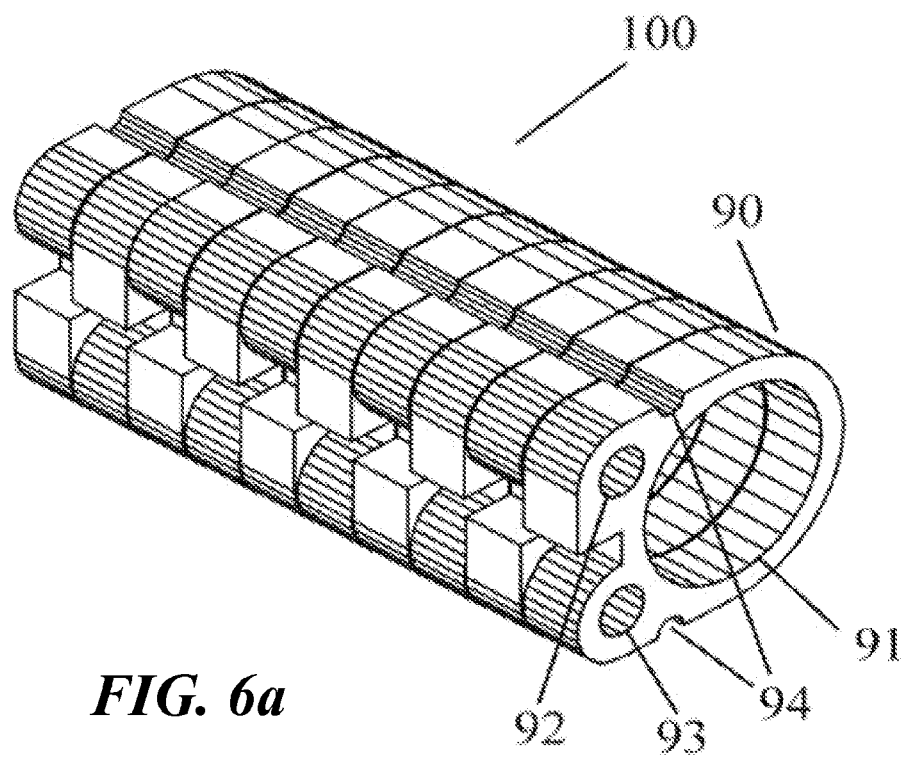
FIGS. 6a) and 6b) illustrate a section of a drift tube of the time-of-flight type assembled from insulating tube segments (90), there being electrically conductive layers between insulating tube segments, said layers being electrically connected with contact strips (96) on a circuit board (95).

FIGS. 6a) and 6b) illustrate a section of a drift tube (100) assembled from insulating tube segments (90) of the same design. The tube segments (90) are preferably made of ceramic and are hard-soldered with a soldering paste. The apertures (91), (92) and (93) of the tube segments (90) are arranged with mirror symmetry so that they are aligned with each other when stacked and form the drift region of the drift tube (100) and two integrated gas channels when assembled.

Soldering with a soldering paste creates thin electrically conductive layers which connect the individual tube segments of the drift tube (100) so they are permanent and gas tight. The electrically conductive layers also enclose the apertures (91) which form the drift region of the drift tube (100) in the assembled state, and serve as field electrodes to generate an axial electric drift field.

Figure 6B:
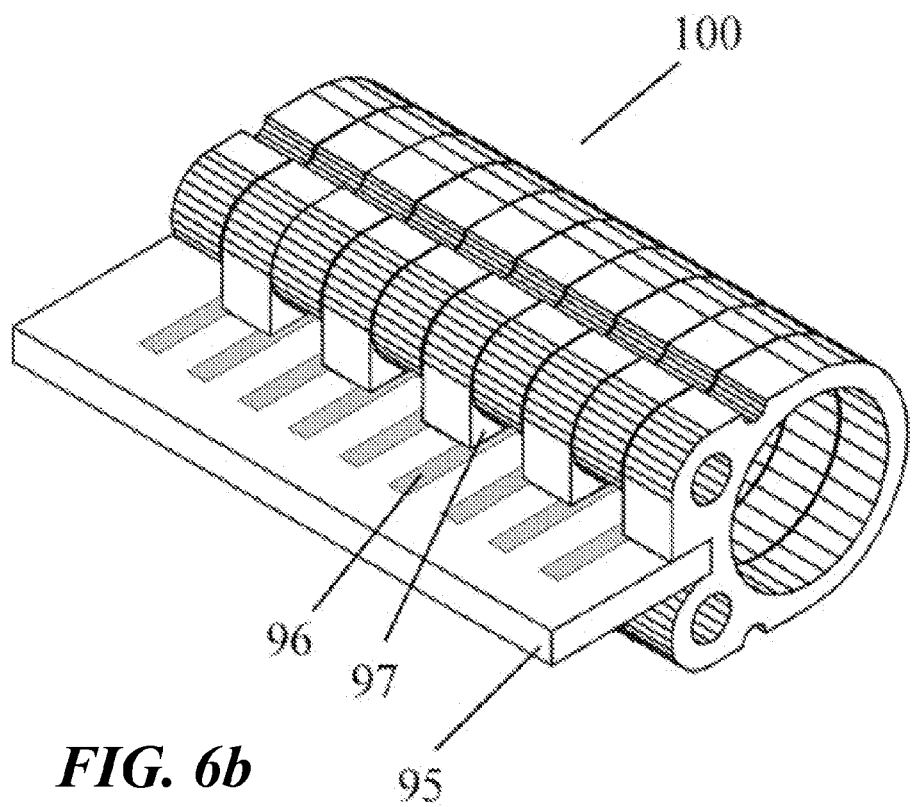

The tube segments (90) of the drift tube (100) are alternately stacked, mirror-inverted. Since the tube segments (90) do not have mirror symmetry, their contact surfaces do not cover each other completely so that the electrically conductive layers are partially uncovered and can be contacted from the outside. The outer contour of the tube segments (90) is shaped so that, when stacked, a slit is formed parallel to the axis of the drift tube into which an electric circuit board (95) can be slid as shown in FIG. 6b). The circuit board (95) has contact strips (96) whose separations correspond to the positions of the electrically conductive layers of the drift tube (100). A contact strip (96) is assigned to every electrically conductive layer (field electrode). The electrical contact is achieved by direct bonding with a conductive adhesive.

The two opposing grooves (94) on the outer edge of the tube segments (90) are for alignment. They are used to stack all parts between two parallel round rods standing vertically on a base plate the same distance apart as the grooves.

The two small apertures (92) and (93) in the tube segments (90) form two integrated gas channels which, in the assembled state, are sealed with respect to each other and to the drift region of the drift tube (100). To connect the integrated gas channels to the drift region it is preferable to insert a connecting metal tube segment (not shown) between two insulating tube segments (90), said segment providing a defined connection between one of the integrated gas channels and the drift region.

With knowledge of the invention, those skilled in the art can design a large number of further embodiments according to the invention.

What is claimed is:

1. A drift tube for use in an ion mobility spectrometer, having an axis and comprising:
    a plurality of tube segments, each of the tube segments having a first aperture and a second aperture, unconnected to the first aperture, both apertures passing through that tube segment;
    means for connecting the tube segments in a stack with gas-tight connections between the tube segments so that the first apertures line up to form a drift region having a constant cross-section and extending along the axis of the drift tube and the second apertures line up to form a gas channel extending parallel to the axis of the drift tube; and
    wherein at least one tube segment having a first aperture and a second aperture connected to the first aperture by a gas channel that extends transverse to the axis of the drift tube, is inserted into the stack so that the first aperture lines up with the drift region and the second aperture lines up with the gas channel and the drift region is connected to the gas channel at the location of that tube segment.

2. A drift tube according to claim 1, wherein each of the tube segments has three apertures passing therethrough and arranged so that, when the tube segments are stacked, the three apertures form a drift region and two gas channels extending along the axis of the drift tube and wherein at least one connecting tube segment is inserted into the stack which connects the two gas channels extending along the axis of the drift tube with each other and with the outer region of the ion mobility spectrometer.

3. A drift tube according to claim 1, wherein each of the tube segments is fabricated from an electrically insulating material.

4. A drift tube according to claim 3, further comprising an electrically conductive layer located between each pair of tube segments in the stack.

5. A drift tube according to claim 4 wherein each electrically conductive layer extends from the first aperture to the exterior of the drift tube where that layer is electrically connected to a voltage supply.

6. A drift tube according to claim 3, wherein tube segments are fabricated from electrically insulating materials and electrically conducting materials.

7. A drift tube according to claim 6 wherein each tube segment fabricated from electrically conductive materials electrically connects the first aperture to the exterior of the drift tube where that tube segment is electrically connected to a voltage supply.

8. A drift tube according to claim 6, wherein the electrically conductive tube segments are fabricated from one of the group consisting of metal, a conductive plastic, a conductive ceramic, a conductively coated plastic and a conductively coated ceramic.

9. A drift tube according to claim 3, wherein the insulating tube segments are fabricated from one of the group consisting of ceramic and plastic.

10. A drift tube according to claim 1, wherein at least one of the tube segments has a contact surface comprising a planar extension which, when the at least one tube segment is assembled in the stack, extends perpendicular to the axis of the drift tube.

11. A drift tube according to claim 1, wherein the stack is mechanically self-supporting.

12. A drift tube according to claim 11, wherein the stack is part of the mechanical support structure of the ion mobility spectrometer.

13. A drift tube according to claim 1, further comprising a filter material and/or doping material located in the gas channel.

14. A drift tube according to claim 1, wherein at least one of the tube segments comprises formed elements or sealing surfaces for contacting pneumatic components or sensors.

* * * * *